(12) United States Patent
Yang

(10) Patent No.: US 12,390,590 B2
(45) Date of Patent: Aug. 19, 2025

(54) INTEGRATED ARTIFICIAL PANCREAS WITH MULTIPLE INFUSION MODES

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 511 days.

(21) Appl. No.: 17/924,363

(22) PCT Filed: May 31, 2021

(86) PCT No.: PCT/CN2021/097160
§ 371 (c)(1),
(2) Date: Nov. 10, 2022

(87) PCT Pub. No.: WO2021/228270
PCT Pub. Date: Nov. 18, 2021

(65) Prior Publication Data
US 2023/0320835 A1 Oct. 12, 2023

(30) Foreign Application Priority Data

Jun. 1, 2020 (WO) ................ PCT/CN2020/093705
Jun. 22, 2020 (WO) ................ PCT/CN2020/097317

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14532* (2013.01); *A61B 5/1473* (2013.01);
(Continued)

(58) Field of Classification Search
CPC ............ A61M 5/1723; A61M 5/14236; A61M 5/14244; A61M 5/14248; A61M 5/1452;
(Continued)

(56) References Cited

U.S. PATENT DOCUMENTS

2002/0029018 A1* 3/2002 Jeffrey ................ A61M 5/1452
604/209
2014/0058349 A1 2/2014 Bazargan et al.
2019/0117881 A1 4/2019 Yang

FOREIGN PATENT DOCUMENTS

CN 103463695 12/2013
CN 104622480 5/2015
(Continued)

OTHER PUBLICATIONS

"International Search Report (Form PCT/ISA/210) of PCT/CN2021/097160", mailed on Jul. 22, 2021, pp. 1-4.

*Primary Examiner* — Mark W. Bockelman
(74) *Attorney, Agent, or Firm* — JCIP GLOBAL INC.

(57) ABSTRACT

An integrated artificial pancreas with multiple infusion modes, includes: drug infusion unit; program unit comprising input end and output end, and the input end comprises a plurality of electrically connective regions for receiving signals of analyte data in the body fluid, after the output end is electrically connected to the power unit, the program unit controls whether the drug infusion unit delivers drugs; and an infusion cannula provided with at least two detecting electrodes, the infusion cannula is the drug infusion channel, the electrodes are disposed on the cannula wall. It takes only one insertion to perform both analyte detection and drug infusion.

19 Claims, 10 Drawing Sheets

(51) Int. Cl.
*A61B 5/145* (2006.01)
*A61B 5/1473* (2006.01)
*A61F 2/02* (2006.01)
*A61M 5/14* (2006.01)
*A61M 5/142* (2006.01)
*A61M 5/145* (2006.01)
*A61M 5/158* (2006.01)
*A61M 5/20* (2006.01)
*G16H 20/17* (2018.01)
*G16H 40/63* (2018.01)

(52) U.S. Cl.
CPC ............ *A61B 5/4839* (2013.01); *A61F 2/022* (2013.01); *A61M 5/14236* (2013.01); *A61M 5/14244* (2013.01); *A61M 5/14248* (2013.01); *A61M 5/1452* (2013.01); *A61M 5/1454* (2013.01); *A61M 5/158* (2013.01); *A61M 5/172* (2013.01); *G16H 20/17* (2018.01); *G16H 40/63* (2018.01); *A61B 2560/0209* (2013.01); *A61B 2562/043* (2013.01); *A61M 5/1413* (2013.01); *A61M 2005/14208* (2013.01); *A61M 2005/14252* (2013.01); *A61M 2005/14268* (2013.01); *A61M 2005/14506* (2013.01); *A61M 2005/1585* (2013.01); *A61M 2005/1726* (2013.01); *A61M 2005/2006* (2013.01); *A61M 2205/0216* (2013.01); *A61M 2205/0233* (2013.01); *A61M 2205/0266* (2013.01); *A61M 2205/33* (2013.01); *A61M 2205/3317* (2013.01); *A61M 2205/3327* (2013.01); *A61M 2205/3553* (2013.01); *A61M 2205/3576* (2013.01); *A61M 2205/3592* (2013.01); *A61M 2205/50* (2013.01); *A61M 2205/502* (2013.01); *A61M 2209/088* (2013.01); *A61M 2230/005* (2013.01); *A61M 2230/20* (2013.01); *A61M 2230/201* (2013.01)

(58) Field of Classification Search
CPC .... A61M 5/1454; A61M 5/158; A61M 5/172; A61M 5/1413; A61M 2005/14208; A61M 2005/14252; A61M 2005/14268; A61M 2005/14506; A61M 2005/1585; A61M 2005/1726; A61M 2005/2006; A61M 2205/0216; A61M 2205/0233; A61M 2205/0266; A61M 2205/33; A61M 2205/3317; A61M 2205/3327; A61M 2205/3553; A61M 2205/3576; A61M 2205/3592; A61M 2205/50; A61M 2205/502; A61M 2209/088; A61M 2230/005; A61M 2230/20; A61M 2230/201; A61M 5/145; A61M 5/20; A61M 5/31; A61M 5/16804; A61B 5/14532; A61B 5/1473; A61B 5/4839; A61B 2560/0209; A61B 2562/043; A61B 5/145; A61F 2/022; G16H 20/17; G16H 40/63

See application file for complete search history.

(56) References Cited

FOREIGN PATENT DOCUMENTS

| CN | 111939387 | 11/2020 |
|---|---|---|
| WO | 2008078319 | 7/2008 |
| WO | 2011064780 | 6/2011 |
| WO | 2013104665 | 7/2013 |
| WO | 2021012796 | 1/2021 |

* cited by examiner

INTEGRATED ARTIFICIAL PANCREAS WITH MULTIPLE INFUSION MODES

CROSS-REFERENCE TO RELATED APPLICATION

This application is a 371 of international application of PCT application serial no. PCT/CN2021/097160, filed on May 31, 2021, which claims the priority benefit of PCT application serial no. PCT/CN2020/093705, filed on Jun. 1, 2020, and PCT application serial no. PCT/CN2020/097317, filed on Jun. 22, 2020 The entirety of each of the above-mentioned patent applications is hereby incorporated by reference herein and made a part of this specification.

TECHNICAL FIELD

The present invention mainly relates to the field of medical instruments, in particular to an integrated artificial pancreas with multiple infusion modes.

BACKGROUND

Diabetes is mainly a metabolic disease caused by abnormal human pancreatic function. Diabetes is a lifelong disease. At present, medical technology cannot cure diabetes. It can only control the occurrence and development of diabetes and its complications by stabilizing blood glucose. The normal human pancreas automatically monitors changes in the body's blood glucose levels and automatically secretes the required insulin. At present, the infusion device for stabilizing blood glucose works by dynamically monitoring the blood glucose changes of the human body by a glucose sensor implanted in the subcutaneous tissue of the human body; and continuously accurately infusing insulin into the subcutaneous tissue of the human body through a medical cannula implanted in the subcutaneous tissue of the human body.

This method requires separately inserting glucose sensor and infusion cannula under the human skin. Even though there are some devices that can integrate the sensor probe and the infusion cannula into one device, the sensor and cannula still need to be separately inserted at different positions, increasing the risk of infection.

Therefore, there is a need in the prior art for an integrated artificial pancreas with multiple infusion modes that can perform both detection and infusion at the same time.

BRIEF SUMMARY OF THE INVENTION

Embodiments of the present invention disclose an integrated artificial pancreas with multiple infusion modes in which multiple electrodes are disposed on an infusion cannula also acted as an infusion channel. It takes only one insertion to perform both analyte detection and drug infusion, thus reducing the risk of infection.

The invention discloses an integrated artificial pancreas with multiple infusion modes, comprising: drug infusion unit, including: at least one drug storage unit; a screw connected to a piston and a driving wheel provided with wheel teeth, respectively, the driving wheel drives the screw to move by rotation, pushing the piston, provided in the drug storage unit, forward; a driving unit at least includes a first driving unit and a second driving unit that cooperate with each other, the second driving unit drives the screw forward; a power unit connected to the first driving unit, the power unit outputs two forces in different directions on the driving unit, making the first driving unit have a variety of different operating modes, thereby making the infusion device have various different infusion increments or infusion rates; a program unit comprising input end and output end, and the input end comprises a plurality of electrically connective regions for receiving signals of analyte data in the body fluid, after the output end is electrically connected to the power unit, according to the received signals of analyte data in the body fluid, the program unit controls the pivot modes of the driving unit to implement whether the drug infusion unit delivers drugs; and an infusion cannula provided with at least two detecting electrodes, the infusion cannula is the drug infusion channel, the electrodes are disposed on the cannula wall, when the infusion cannula is installed to the working position, the infusion cannula is connected with the drug infusion unit, the drug can then be injected into the body through the infusion cannula, and the different electrodes are electrically connected to different electrically connective regions respectively, inputting signal of analyte data in the body fluid to the program unit.

According to one aspect of this invention, the electrodes are located on the outer surface of the cannula wall or in the cannula wall.

According to one aspect of this invention, the electrodes are located on the outer surface of the cannula wall, and when the infusion cannula is installed to the working position, different electrodes are directly electrically connected to different electrically connective regions, respectively.

According to one aspect of this invention, the electrodes are located on the subcutaneous part of the outer surface of the cannula wall, and the outer surface of the cannula wall is further provided with electrode leads electrically connected to the electrodes, and when the infusion cannula is installed to the working position, different electrode leads are electrically connected to different electrically connective regions, respectively.

According to one aspect of this invention, the infusion cannula includes an inner layer cannula and at least one outer layer cannula, and the outer layer cannulas are disposed outside the inner layer cannula, and the inner layer cannula is used for drug infusion.

According to one aspect of this invention, at least one electrode is provided between the outer wall of the inner layer cannula and the outermost cannula.

According to one aspect of this invention, when the infusion cannula is installed to the working position, the electrode located on the outer wall surface of the inner layer cannula is entirely exposed in the subcutaneous tissue fluid, or covered in whole or in part by the outer layer cannulas.

According to one aspect of this invention, when the electrode located on the outer wall surface of the inner layer cannula is covered in whole or in part by the outer layer cannulas, the material of the outer layer cannula walls is permeable membrane or a semi-permeable membrane.

According to one aspect of this invention, the electrodes include working electrode and auxiliary electrode, and the number of the working electrode(s) and the auxiliary electrode(s) is one or more, respectively.

According to one aspect of this invention, the auxiliary electrode is counter electrode, or the auxiliary electrode includes counter electrode and reference electrode.

According to one aspect of this invention, a plurality of electrodes form one or more electrode combinations, each electrode combination comprising working electrode and auxiliary electrode, the program unit choosing one or more electrode combinations to detect analyte data in body fluid.

According to one aspect of this invention, the input end is an elastic member, and the elastic member comprises one of or a combination of conductive strip, oriented conductive silica gel, conductive ring and conductive ball.

According to one aspect of this invention, the drug infusion unit includes a plurality of infusion subunits, the plurality of infusion subunits being electrically connected to the output ends, respectively, and the program unit controlling whether each infusion subunit delivers drugs.

According to one aspect of this invention, the integrated artificial pancreas with multiple infusion modes is composed of a plurality of parts, the drug infusion unit and the program unit are arranged in different parts, and the different parts are connected by waterproof plugs.

According to an aspect of the present invention, the operating mode of the first driving unit includes the amplitude of the unidirectional movement, the amplitude of the reciprocating movement or the movement rate, therefore a variety of different operating modes of the first driving unit include different unidirectional movement or reciprocating movement, or various different movement rates.

According to an aspect of the present invention, the first driving unit includes at least one driving end, and the second driving unit includes at least one driving wheel provided with wheel teeth, and the driving end pushes the wheel teeth forward to rotate the driving wheel.

According to an aspect of the present invention, the driving unit further includes a rotating shaft, the first driving unit includes at least two driving ends, and the second driving unit includes two fixedly connected driving wheels, and each driving wheel cooperates with at least one driving end.

According to an aspect of the present invention, it further includes a base on which the second driving unit is movably assembled, and the base and the second driving unit are frictional fit.

According to an aspect of the present invention, it further includes a position limited member which is movably assembled on the base to limit the position of the second driving unit, and the position limited member and the second driving unit are frictional fit.

DETAILED DESCRIPTION

Figure 1:
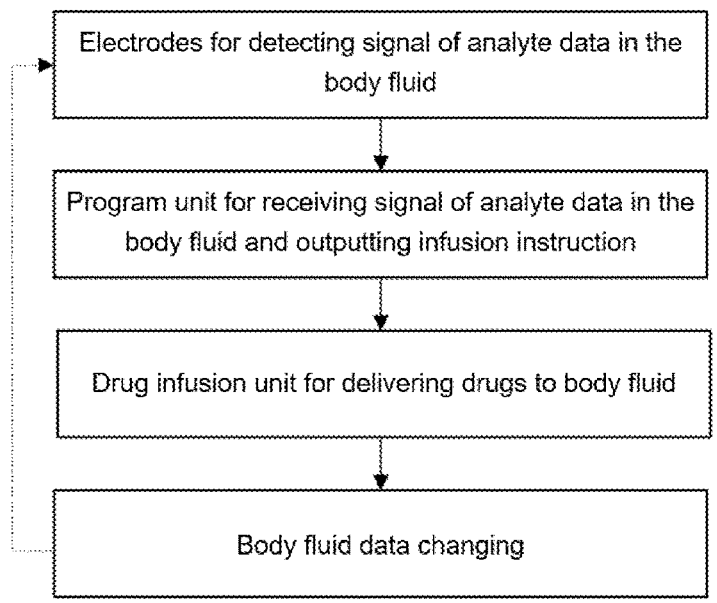
FIG. 1 is a flow chart of the operation of an integrated artificial pancreas with multiple infusion modes according to an embodiment of the present invention.

As described above, in the prior art device, the detection and the infusion are performed separately to control the analyte level in the body fluid, and it is necessary to puncture at multiple positions on the skin, thereby increasing the pain of the user and increasing the risk of infection.

The study found that the cause of the above problems is that the sensor detection device and the infusion device are two independent units. Or even if the two are designed into a single structure, multiple puncture positions are still required on the body surface.

In order to solve this problem, the present invention provides an integrated artificial pancreas with multiple infusion modes, the infusion cannula is used for detecting analyte data and a drug infusion channel. And it can perform detection and infusion with only one puncture.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in the following description of the drawings.

FIG. 1 is a flow chart showing the operation of an integrated artificial pancreas with multiple infusion modes according to an embodiment of the present invention.

The integrated artificial pancreas with multiple infusion modes of the embodiment of the invention comprises three basic parts: electrodes, a program unit and a drug infusion unit. The body fluid analyte data is obtained by the electrodes and converted into an electrical signal. Electrical signals are passed to the program unit via electrodes and/or electrode leads. After analyzing the body fluid analyte data signal, the program unit, through the power unit, sends a signal to the drug infusion unit controlling whether to perform a drug infusion, thereby stabilizing the body fluid parameters. The body fluid analyte data are detected by the electrodes in real time, and the cycle of detection and infusion is without interruption. This process does not require human intervention and is done directly through program analysis to control the stability of body fluid parameters.

Figure 2:
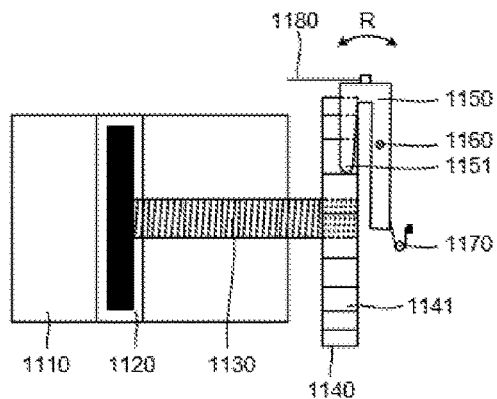
FIG. 2 is a schematic diagram of an internal structure of an infusion unit according to an embodiment of the present invention.

FIG. 2 is a schematic diagram of the internal structure of the infusion unit according to an embodiment of the present invention.

The internal structure of the infusion unit mainly includes a reservoir 1110, a piston 1120, a screw 1130, a driving unit and a power unit.

The reservoir 1110 is used to store drugs which include, but are not limited to, insulin, glucagon, antibiotics, nutrient solutions, analgesics, morphine, anticoagulants, gene therapy drugs, cardiovascular drugs or chemotherapy drugs.

The piston 1120 is used to infuse liquid drug into the body.

The screw 1130 is connected to the piston 1120, thereby pushing the piston 1120 to advance, achieving the purpose of drug infusion. The screw 1130 is a rigid screw or a flexible screw. When the screw 1130 is a flexible screw, the screw 1130 may be designed to be curved. In one embodiment of the invention, the flexible screw is formed by a plurality of threaded sub-units movably connected one by one.

The driving unit, used to drive the screw 1130 forward, includes a first driving unit and a second driving unit that cooperate with each other. The second driving unit is connected to the screw 1130. Here, the cooperation means that when the first driving unit operates in a certain manner or mode, the second driving unit will implement an associated operating manner or mode to achieve the goal of driving the screw 1130 forward and completing the drug infusion. The meaning of cooperation with each other below is the same as here.

It should to be noted here that the operating manner and operating mode belong to different technical concepts. The operating manner refers to the specific working method or working form, such as unidirectional movement or reciprocating movement, of the first driving unit. However, the operating mode represents the effect, such as the movement amplitude or movement rate, brought about by the operating manner of the first driving unit. The unidirectional movement includes linear unidirectional movement or unidirectional rotation, while the reciprocating movement includes linear reciprocating movement or reciprocating rotation.

The embodiments of the present invention do not limit the types or structural relationships of the first driving unit and the second driving unit, as long as the condition of completing the drug infusion through their cooperation is satisfied. As in one embodiment of the present invention, both the first driving unit and the second driving unit are gears. As in another embodiment of the present invention, the first driving unit is a linear reciprocating pawl, while the second driving unit is a ratchet. As in another embodiment of the present invention, the first driving unit is an airbag, and the second driving unit is a driving rod which can directly pushes the screw 1130 forward. And the contraction and relaxation of the airbag drive the driving rod to reciprocate. As in yet another embodiment of the present invention, the driving unit further includes one or more auxiliary driving units connected to the first driving unit or the second driving unit, and the first driving unit and the second driving unit may not be in direct contact or connected directly. The auxiliary driving unit transmits the operating manner or operating mode of the first driving unit to the second driving unit, thereby making the second driving unit implement the operating manner or operating mode associated with the first driving unit.

Since the first driving unit is a driving structure and the second driving unit is a driven structure, the power unit outputs driving power to the first driving unit which will have a variety of different operating modes, such as different unidirectional movement amplitude, reciprocating movement amplitude or movement rate. And the connection method between the power unit and the first driving unit includes mechanical connection or electrical connection.

Specifically, in the embodiment of the present invention, the power unit includes a first power unit and a second power unit which are electrically or mechanically connected to and apply driving power to the first driving unit, respectively. The operating mode of the first driving unit includes unidirectional movement or reciprocating movement, which will be described in detail below combined with different embodiments.

The first driving unit includes at least one driving member 1150, and the second driving unit includes at least one driving wheel 1140 provided with wheel teeth 1141. The driving unit further includes a rotating shaft 1160, and the driving member 1150 includes at least one driving end 1151. Specifically, in the embodiment of the present invention, the first driving unit is one driving member 1150 including only one driving end 1151, and the second driving unit is one driving wheel 1140, and the first power unit is an advancing member 1180 while the second power unit is a reset member 1170, as shown in FIG. 2. Preferably, for being pushed more easily, the driving wheel 1140 is a ratchet with ratchet teeth.

The reset member 1170 includes an electrically driven linear actuator, an electrically heated linear actuator, or an elastic member that can automatically reset the driving member 1150 without using an external force. The type of elastic members includes, but is not limited to, at least one compression spring, extension spring, torsion spring, elastic sheet, elastic plate, elastic rod, elastic rubber, and the like. Specifically, in the embodiment of the present invention, the reset member 1170 is a torsion spring which is more conducive to reset the driving member 1150.

In another embodiment of the present invention, the reset member 1170 is an electrically driven linear actuator or an electrically heated linear actuator, such as a shape memory alloy. After being energized, the physical form of the material of the linear actuator changes, which makes it shrinkage deformation, thereby outputting driving power to pivot the driving member 1150. The higher the current is, the larger shrinkage deformation is, and the greater the driving power outputs. Obviously, when the current is constant, the driving power output by the linear actuator is constant. Therefore, the linear actuator can output a stable and controllable driving power, which makes the infusion process stable and controllable, enhancing the user experience.

The advancing member 1180, an electrically driven linear actuator or an electrically heated linear actuator, directly applies driving power to the driving member 1150. Specifically, in the embodiment of the present invention, the advancing member 1180 is a shape memory alloy.

The program unit (not shown) is connected to the power unit. In the embodiment of the present invention, the program unit applies driving power to the advancing member 1180, which makes the driving member 1150 drive the driving end 1151 to advance the wheel teeth 1141, pivoting the driving wheel 1140, thereby making the infusion unit perform drug infusion.

Figure 3:
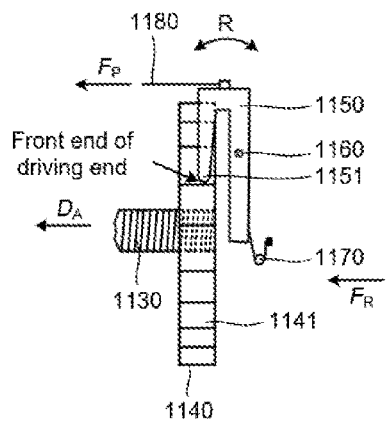
FIG. 3 is a partial top view of the driving unit and the power unit in FIG. 2.

FIG. 3 is a partial top view of the driving unit and the power unit in FIG. 2.

The principle of the driving member 1150 driving the driving wheel 1140 to rotate in the embodiment of the present invention is as follows. When the program unit controls the advancing member 1180 to pull the driving member 1150 by force $F_P$, the driving member 1150 rotates counter-clockwise around the rotating shaft 1160, driving the driving end 1151 to push the wheel teeth 1141 forward, thereby making the driving wheel 1140 rotate, which makes the screw 1130 advance in the $D_A$ direction and makes the infusion unit perform drug infusion. At this time, the reset member 1170 is an elastic member which builds a gradually increasing elastic force $F_R$. When the advancing member 1180 stops applying force and under the action of the elastic force $F_R$, the driving member 1150 rotates clockwise around the rotating shaft 1160. And the driving end 1151 stops pushing the wheel teeth 1141, therefore the driving wheel 1140 stops rotating, and the screw 1130 stops advancing, so that the infusion unit does not proceed drug infusion. The driving end 1151 slides and resets on the surface of the wheel teeth 1141 until the driving member 1150 stops rotating, which makes the driving member 1150 complete one reciprocating rotation R. By analogy, the driving member 1150 can complete multiple reciprocating rotations. Obviously, when the infusion unit of the embodiment of the present invention is in operation, the rotating manner of the driving wheel 1140 is intermittent rotation, that is, a manner of rotation-stop-rotation-stop- . . . . The meaning of intermittent rotation below is the same as here.

Figure 4:
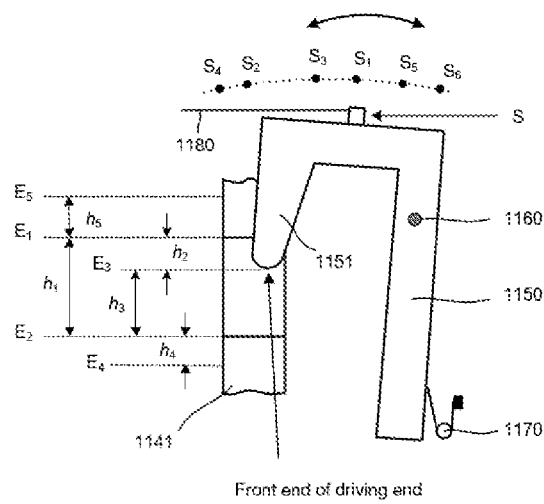
FIG. 4 is a schematic diagram of the reciprocating rotation amplitude of the driving member according to an embodiment of the present invention.

FIG. 4 is a schematic diagram of the reciprocating rotation amplitude of the driving member 1150 according to an embodiment of the present invention.

Referring to FIG. 4, the principle of the driving member 1150 implementing two reciprocating rotation amplitudes according to the embodiment of the present invention is as follows. The program unit controls the magnitude of the force output of the advancing member 1180, and the reset member 1170 implements resetting function, which makes the driving member 1150 to reciprocate and makes the driving end 1151 advance and reset. $E_n$ represents the position reached by the front end of the driving end, such as $E_1$, $E_2$, $E_3$, $E_4$, $E_5$. $h_n$ represents the distance between two different positions $E_n$. $S_n$ represents the different positions of the point S of the force output by the advancing member 1180 during the reciprocating rotation, and the dotted arc in FIG. 4 represents the trajectory of S, therefore, $S_1$, $S_2$, $S_3$, $S_4$, $S_5$ corresponds with $E_1$, $E_2$, $E_3$, $E_4$, $E_5$, respectively. Obviously, the movement distance between different $S_n$ can be used to represent the rotation amplitude of the driving member 1150. Specifically, in the embodiment of the present invention, $h_1$ is the pitch of gear tooth, and $h_1=3h_2$.

When the advancing member 1180, according to the instruction, makes the driving end 1151 to advance the wheel teeth 1141 from the $E_1$ to the $E_2$ position, the advancing member 1180 stops outputting power, and the reset member 1170 starts to work until resetting the driving end 1151 to the $E_3$ position, which makes the driving member 1150 complete the first reciprocating. The rotation amplitude of the driving member 1150 is $S_1$-$S_2$ and $S_2$-$S_3$. During the first reciprocating rotation, the front end of the driving end pushes a tooth forward by a distance $h_1$, the drug infusion volume is $V_1$, and its reset distance is $h_3$. At this time, the infusion volume $V_1$ is regarded as the infusion increment in this first mode. When the next driving is performed, the advancing member 1180 outputs force again. During the advancing distance $h_3$ of the driving end, the driving wheel 1140 does not rotate, nor the drug infusion of the infusion unit. When the front end of the driving end reaches the $E_2$ position and continues to advance by a distance of $h_4$, the front end of the driving end pushes the wheel teeth 1141 to the $E_4$ position, the driving wheel 1140 rotates, implementing the drug infusion. When the advancing member 1180 stops outputting the force, the reset member 1170 resets the driving end 1151 to a certain position, such as the $E_5$ position, therefore, the driving member 1150 completes the second reciprocating rotation, and the driving member 1150 rotates by $S_3$-$S_4$ and $S_4$-$S_5$. During the second reciprocating rotation, the forward distance of the front end of the driving end is $(h_3+h_4)$, and the drug infusion volume is $V_2$. At this time, the infusion volume $V_2$ is the infusion increment in this second mode. Obviously, the driving member 1150 only drives the driving wheel 1140 to rotate under the rotation amplitudes $S_1$-$S_2$ and $S_2$-$S_4$ in these two modes. For the rotation amplitude $S_1$-$S_2$ is greater than the rotation amplitude $S_2$-$S_4$ (or $h_1 > h_4$), $V_1 > V_2$. Therefore, the infusion unit of the embodiment of the present invention has two different infusion increments.

By analogy, the distance between $E_1$, $E_2$, $E_3$, $E_4$, $E_5$ can be arbitrarily selected, such as $h_1=h_2$, $h_1=2h_2$, $h_1=4h_2$, etc., the infusion unit has a variety of different infusion increments. Or the force point S can also reaches to the $S_6$ position, and $S_4$ and $S_6$ may not be the limit positions for the rotating of the driving member 1150, which is not specifically limited herein.

It should be noted that, as described above, in the embodiment of the present invention, the infusion unit does not necessarily implement drug infusion when the driving end 1151 advances. Only when the driving end 1151 pushes the wheel teeth 1141 forward, the infusion device does.

Each rotation amplitude of the driving member 1150 corresponds with an infusion increment. Therefore, a variety of different rotation amplitudes of the driving member 1150 make the infusion unit have a variety of different infusion increments. Taking insulin as an example, the infusion increment range of the infusion unit in the embodiment of the present invention is 0.0005 U~0.25 U (here, the infusion increment range includes endpoint values, that is, the infusion increment includes 0.0005 U and 0.25 U). In some embodiments of the present invention, the infusion increment of the infusion unit may includes 0.001 U, 0.0025 U, 0.005 U, 0.0075 U, 0.01 U, 0.025 U, 0.05 U, 0.075 U, 0.1 U, etc. Specifically, in the embodiment of the present invention, the infusion increment of the infusion unit includes 0.005 U, 0.0075 U, 0.01 U, 0.025 U, and 0.05 U.

It should be noted that in the embodiment of the present invention, the insulin concentration is 100 U/ml. In other embodiments, the insulin concentration may also be 200 U/ml, 400 U/ml, etc., which is not specifically limited here.

It should be noted here that when $h_1=h_2$, the infusion increment of the infusion unit always maintains $V_1$ with the rotation amplitude always maintaining $S_1$-$S_2$ and $S_2$-$S_1$, which makes the infusion relatively stable.

Another embodiment of the present invention can also increase the frequency of the force output by the advancing member 1180 to increase the frequency of the reciprocating rotation of the driving member 1150, thereby increasing the infusion rate of the infusion unit. Therefore, the infusion unit in the embodiments of the present invention can all change the power output frequency of the power unit to make them have multiple infusion rates. Here, the change of the power output frequency can change the rate of the unidirectional movement, the frequency of intermittent movement, the rate of any single movement, the rate of reciprocating movement, or the frequency of reciprocating movement, which will be described in detail below.

Figure 5A:
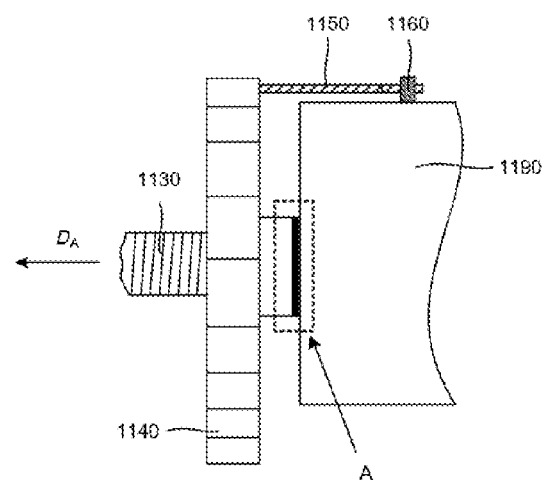
FIG. 5a-FIG. 5b are schematic diagrams of frictional fit between a driving wheel and a base or a position limited member according to an embodiment of the present invention.
Figure 5B:
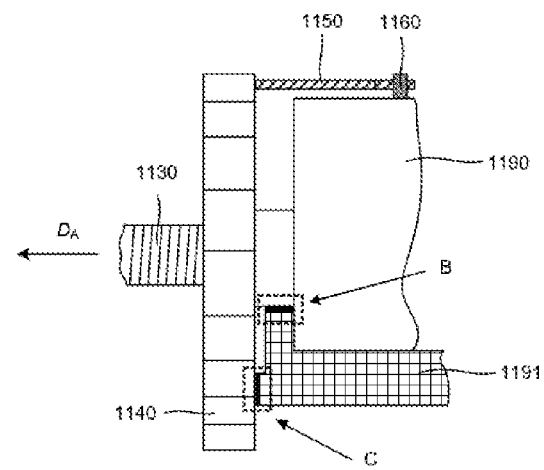

FIG. 5a and FIG. 5b are schematic diagrams of the driving wheel 1140 and the base 1190 or the position limited member 1191 according to an embodiment of the present invention. FIG. 5a and FIG. 5b are front views of FIG. 3.

The movement of the second driving unit can directly drive the screw forward to complete the drug infusion. Therefore, when the first driving unit does not actually drive, the second driving unit should stop moving. As in the embodiment of the present invention, when the driving end 1151 slides on the surface of the wheel teeth 1141, the driving end 1151, contact with the wheel teeth 1141, applies a certain pressure to the driving wheel 1140 to ensure the non-rotating of the driving wheel 1140. However, it is obvious that due to the structural features of the wheel teeth 1141 and the circumference of the driving wheel 1140, the pressure applied by the driving end 1151 is not equal at different positions. Therefore, when the driving end 1151 slides (reset movement or sliding forward) on the surface of the wheel teeth 1141, the driving wheel 1140 may rotate forward or reverse, which affects the accuracy of the drug infusion volume and brings safety risk.

In an embodiment of the present invention, the second driving unit is movably assembled on the base 1190 remaining in frictional engagement. Here, the friction fit means a certain friction force preset between two mutually moving structures, so as to the meaning of the following friction fit. In another embodiment of the present invention, the infusion unit further includes a position limited member movably assembled on the base 1190 to limit the position of the second driving unit in a frictional engagement way.

As shown in FIG. 5a, the driving wheel 1140 is movably assembled on the base 1190 remaining in frictional engagement. In the embodiment of the present invention, the frictional force of the relative movement between the driving wheel 1140 and the base 1190 is applied or increased at the position A, indicated by the dotted frame to ensure that when the driving end 1151 slides on the surface of the wheel teeth 1141, the driving wheel 1140 stops rotating.

As shown in FIG. 5b, in another embodiment of the present invention, the infusion unit further includes a position limited member 1191 that is movably assembled on the base 1190 to limit the position of the driving wheel 1140. The position limited member 1191 is in friction fit with the driving wheel 1140 at position B or position C, as indicated by the dotted frame. Similarly, in the embodiment of the present invention, the position limited member 1191 increases the frictional force that the driving wheel 1140 receives when rotating, also ensuring that the driving wheel 1140 stops rotating when the driving end 1151 slides on the surface of the wheel teeth 1141.

Other embodiments of the present invention do not limit the position of the above friction fit, as long as the condition for increasing or applying the friction force received by the second driving unit during movement is satisfied. For example, the friction force can also be applied on both sides of the driving wheel 1140 at the same time. The embodiment of the present invention neither limits the material of the position limited member 1191. For example, the position limited member 1191 is an elastic member, a plastic member or a metal member.

Other embodiments of the present invention may increase the pressure of the driving end 1151 on the wheel teeth 1141 instead of providing the above-mentioned friction fit, which can increase the maximum static friction of the driving wheel 1140 and ensure the non-rotating of the driving wheel 1140 when the driving end 1151 slides on the surface of the wheel teeth 1141.

FIG. 6a-FIG. 6d are schematic diagrams of the driving member 1150, the rotating shaft 1160, the reset member 1170, and the advancing member 1180 according to other embodiments of the present invention.

Figure 6A:
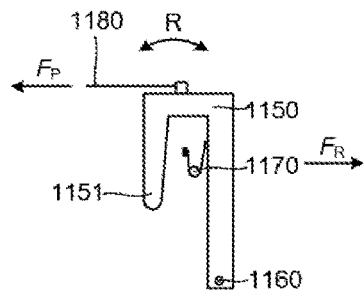
FIG. 6a-FIG. 6d are schematic diagrams of a driving member, a rotating shaft, a reset member and an advancing member according to an embodiment of the present invention.
Figure 6B:
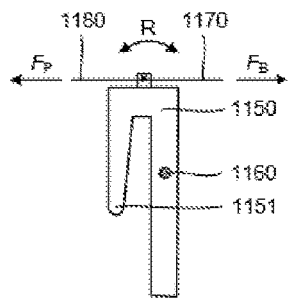
Figure 6C:
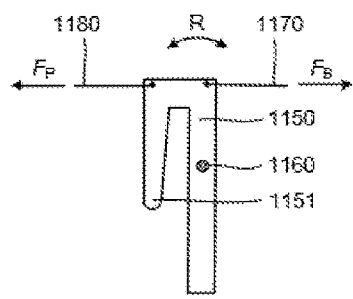
Figure 6D:
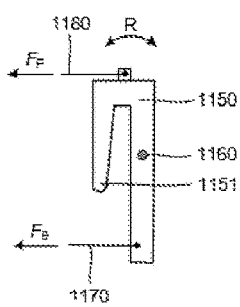

As described above, the power unit outputs different forces on the first driving unit to make the first driving unit have multiple different operating modes. Since the force is a vector, different force means different magnitude or direction, or that the force is applied at different positions of the first driving unit. In the embodiment of the present invention, the power unit applies force in different linear directions to the first driving unit. In FIG. 6b-FIG. 6d, the reset member 1170 is a shape memory alloy. Obviously, the $F_P$ direction is parallel to the $F_R$ and $D_A$ direction. Such a parallel design can make full use of the space and structural relationship inside the device, making the internal structure more compact.

It should be noted here that because the shape memory alloy is inelastic, the driving member 1150 cannot be automatically reset after stopping the advance only in the case that the reset member 1170 is energized by the program unit to build power to reset the driving member 1150.

Since the force can change the movement state of the first driving unit, in other embodiments of the present invention, the power unit can also apply a force that makes the first driving unit to have different rotation rates or different rotation modes, which will be described in detail below.

Figure 7A:
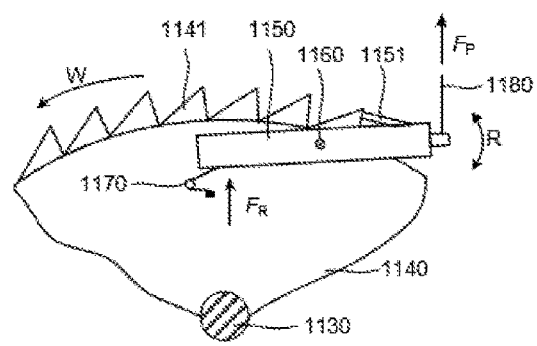
FIG. 7a-FIG. 7b are schematic diagrams of the structure in which the power direction of the advancing member is not parallel to the advancing direction of the screw according to another embodiment of the present invention.
Figure 7B:
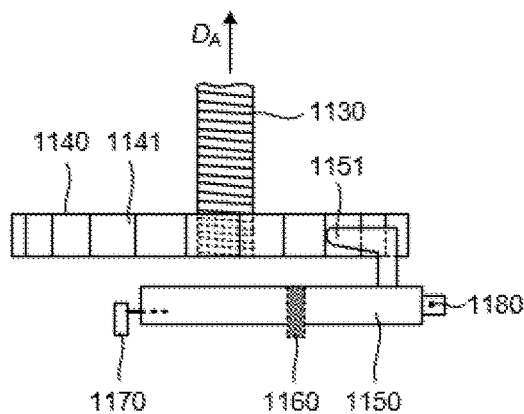

FIG. 7a and FIG. 7b are schematic diagrams of the structure in which the force $F_P$ direction of the advancing member 1180 is not parallel to the advancing direction $D_A$ of the screw 1130 according to an embodiment of the present invention.

The $F_P$ direction may not be parallel with the $F_R$ direction, which is not specifically limited here, as long as the purpose of reciprocating rotation of the driving member 1150 can be achieved. As shown in FIG. 7a and FIG. 7b, the direction of the pulling force $F_P$ of the advancing member 1180 is perpendicular to the advancing direction $D_A$ of the screw 1130. The rotating shaft 1160 and the reset member 1170 are provided on a base (not shown). As described above, the driving member 1150 reciprocally rotates in the R direction to drive the driving end 1151 to push the wheel teeth 1141, rotating the driving wheel 1140 in the W direction, thereby driving the screw 1130 to advance in the $D_A$ direction. The working principle and operating mode of the driving member 1150 are the same as described above.

Figure 8:
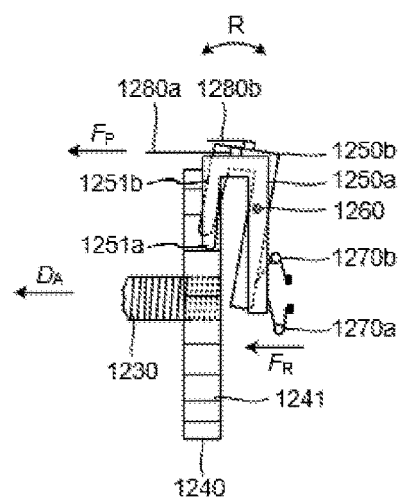
FIG. 8 is a schematic diagram of a driving unit including two driving members and a rotating shaft according to yet another embodiment of the present invention.

FIG. 8 is a schematic diagram of a driving unit including two driving members and a rotating shaft 1260 according to another embodiment of the present invention. The two driving members share the same rotating shaft 1260.

As shown in FIG. 8, the two driving members 1250a and 1250b can independently operate around the rotating shaft 1260, which means that each driving member 1250a and 1250b can independently push the wheel teeth 1241 forward. The independent working principle and operating mode of the driving member 1250a or 1250b are the same as that described above.

The program unit of the embodiment of the present invention can also control the power output of the advancing members 1280a and 1280b, and combined with the reset members 1270a and 1270b, they can make the driving ends 1251a and 1251b alternately push the wheel teeth 1241 forward, thereby rotating the driving wheel 1240 to implement the drug infusion.

In the embodiment of the present invention, as long as a certain driving end reaches the driving position, the wheel teeth 1241 can be pushed forward. The driving position here refers to the position where the driving end can, but not necessarily, push the wheel teeth forward, as shown in the positions $E_1$ and $E_2$ in FIG. 4, and the following driving position has the same meaning as here.

In operation, by controlling the rotation amplitude of the driving members 1250a and 1250b, the driving ends 1251a and 1251b alternately push the wheel teeth 1241 forward, thereby enabling the infusion unit to have a variety of different infusion increments.

Figure 9:
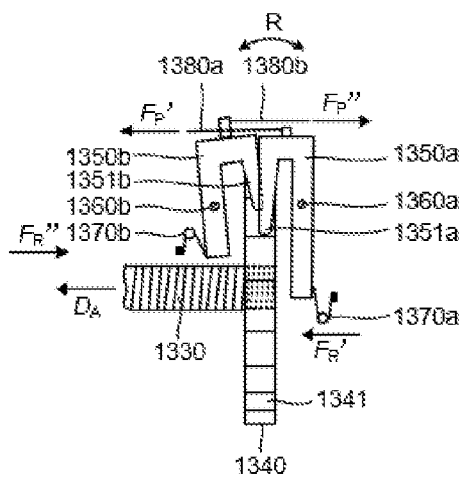
FIG. 9 is a schematic view of a driving unit including two rotating shafts and two driving members according to yet another embodiment of the present invention.

FIG. 9 is a schematic diagram of a driving unit including two rotating shafts and two driving members according to yet another embodiment of the present invention.

As shown in FIG. 9, the two driving members 1350a and 1350b reciprocally rotate around the rotating shafts 1360a and 1360b, respectively. The two driving members 1350a and 1350b and the rotating shafts 1360a and 1360b are respectively disposed on both sides of the driving wheel 1340. The driving members 1350a and 1350b reciprocally rotate under the force of $F_P'$, $F_R'$ and the force of $F_P''$, $F_R''$, respectively, to drive the driving ends 1351a and 1351b forward or reset. The driving members 1350a or 1350b have different rotation amplitudes, and the driving members 1350a or 1350b can also independently push the wheel teeth 1341 following working principles and operating modes described above. Similarly, the driving members 1350a and 1350b can also cooperate with each other to alternately push the wheel teeth 1341 forward.

Figure 10A:
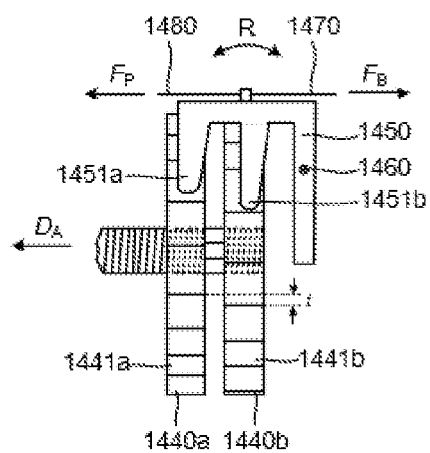
FIG. 10a-FIG. 10b are schematic diagrams of two driving ends of a driving member cooperating with two driving wheels according to yet another embodiment of the present invention.
Figure 10B:
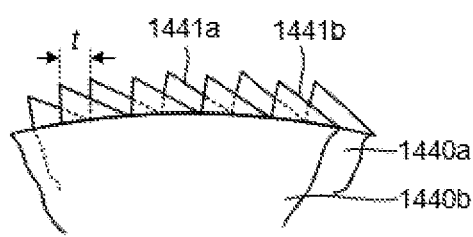

FIG. 10a and FIG. 10b are schematic diagrams of two driving ends 1451a and 1451b of a driving member 1450 cooperating with two driving wheels 1440a and 1440b respectively according to yet another embodiment of the present invention. FIG. 10b is a right side view of the partial wheel teeth structure of the driving wheels 1440a and 1440b in FIG. 10a.

As shown in FIG. 10a and FIG. 10b, in the embodiment of the present invention, the driving member 1450 includes two driving ends 1451a and 1451b disposed left and right, while the second driving unit includes two fixedly connected driving wheels 1440a and 1440b also disposed on the left and right (that is, two driving wheels can move simultaneously). The driving ends 1451a and 1451b cooperate with the driving wheels 1440a and 1440b, respectively, and the rotating shaft 1460 is disposed on the same side of two driving wheels 1440a and 1440b. Both the advancing member 1480 and the reset member 1470 of the embodiment of the present invention are shape memory alloys, and the driving end 1451a or 1451b can respectively push the wheel teeth 1441a or 1441b forward. Their working principles and operating modes are consistent with the foregoing.

In addition to driving end 1451a or 1451b operating independently, the embodiment of the present invention can also adjust the distance between the front ends of the driving ends 1451a and 1451b, or adjust the offset degree of the wheel teeth 1441a and 1441b to make two driving ends 1451a and 1451b cooperate with each other. Preferably, in the embodiment of the present invention, the wheel teeth 1441a and 1441b are offset with degree t, as shown in FIG. 10a and FIG. 10b. The following teeth offset of two driving wheels have the same meaning here.

Obviously, in the embodiment of the present invention, two driving ends 1451a and 1451b reciprocate synchronously. As shown in FIG. 10a, when the previous forward movement is completed, the driving member 1450 starts a reset movement, the driving end 1451a reaches the driving position before the driving end 1451b, so the driving end 1451a can be used to start the next forward movement instead. Or the driving member 1450 continues the reset movement until the driving end 1451b reaches the next driving position to start the next forward movement. Of course, the driving member 1450 may continue to be reset for a much larger distance, as described above.

Therefore, by controlling the rotation amplitude of the driving member 1450, the driving end 1451a or 1451b can individually push the corresponding wheel teeth 1441a or 1441b forward, or the driving end 1451a or 1451b alternately pushes the wheel teeth forward, making the infusion unit have multiple infusion increments.

Figure 11A:
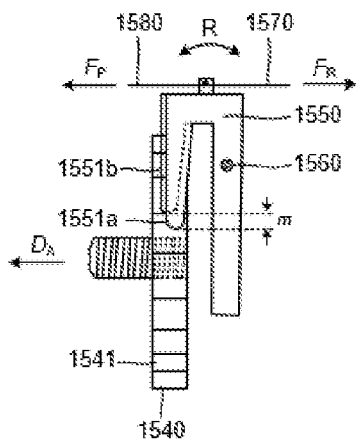
FIG. 11a-FIG. 11b are schematic diagrams of a driving member including two driving ends disposed up and down according to yet another embodiment of the present invention.
Figure 11B:
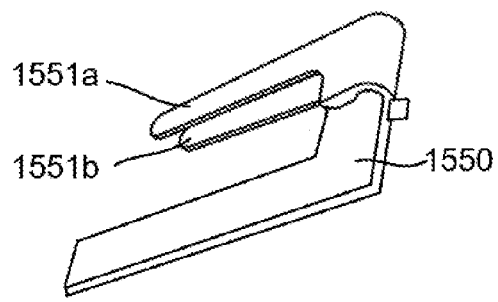

FIG. 11a and FIG. 11b are still another embodiment of the present invention in which the driving member 1550 includes two driving ends 1551a and 1551b disposed up and down, and driving ends 1551a and 1551b cooperate with the same driving wheel 1540. FIG. 11b is a perspective diagram of the driving member 1550 in FIG. 11a.

As shown in FIG. 11a and FIG. 11b, the driving member 1550 includes two driving ends 1551a and 1551b disposed up and down cooperating with the same driving wheel 1540, so the driving ends 1551a and 1551b reciprocate synchronously. The front ends of the driving ends 1551a and 1551b are not level with a certain distance m, therefore, the two cannot simultaneously push the wheel teeth 1541 forward, as shown in FIG. 11a. When the driving end 1551b finishes the last forward movement, the driving member 1550 performs a reset movement, obviously making the driving end 1551a reach the next driving position before the driving end 1551b. The driving end 1551a can be used to push the wheel teeth 1541 forward to start the next forward movement. Or the driving member 1550 continues the reset movement until the driving end 1551b reaches the next driving position to start the next forward movement. Of course, the driving ends 1551a and 1551b can also reset to a much larger distance, as described above.

Therefore, by controlling the power output by the advancing member 1580 or the reset member 1570, the driving member 1550 has different rotation amplitudes, which makes the driving end 1551a or 1551b individually push the wheel teeth 1541 forward or the two alternately push the wheel teeth 1541 forward, thereby making the infusion unit have a variety of different infusion increments.

Figure 12A:
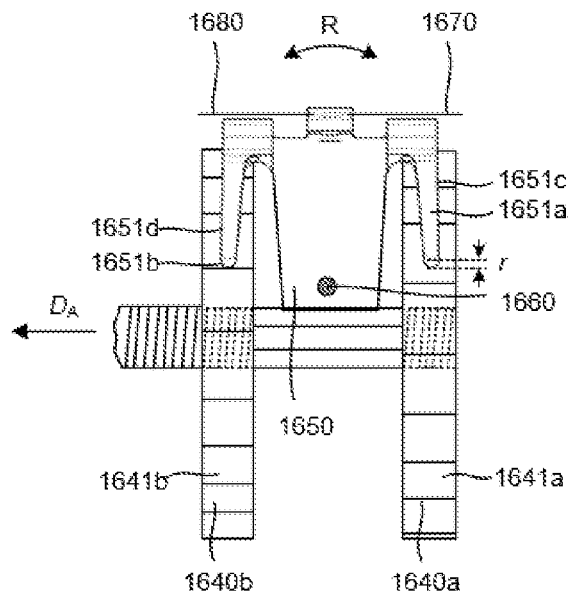
FIG. 12a-FIG. 12b are schematic structural views of a driving member disposed between two driving wheels according to yet another embodiment of the present invention.
Figure 12B:
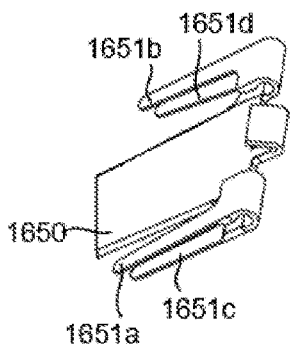

FIG. 12a and FIG. 12b are schematic diagrams of a driving member 1650 disposed between two driving wheels 1640a and 1640b according to yet another embodiment of the present invention. FIG. 12b is a perspective diagram of the driving member 1650 in FIG. 12a.

As shown in FIG. 12a and FIG. 12b, the driving member 1650 includes four driving ends 1651a, 1651b, 1651c and 1651d, and the second driving unit includes two fixedly connected driving wheels 1640a and 1640b. The driving ends 1651a and 1651c are disposed on one side of the driving member 1650 and cooperate with the driving wheel 1640a, while the driving ends 1651b and 1651d are disposed on the other side to cooperate with the driving wheel 1640b. In the embodiment of the present invention, both the first power unit 1680 and the second power unit 1670, making the driving member 1650 reciprocate, are shape memory alloys.

Specifically, in the embodiment of the present invention, the driving member 1650 can drive the driving end in both directions of the reciprocating rotation to push the wheel teeth forward for drug infusion. When the driving member 1650 rotates clockwise, the driving end 1651b or 1651d can push the wheel teeth 1641b forward, thereby making driving wheels 1640a and 1640b rotate synchronously and the infusion unit perform drug infusion, while driving ends 1651a and 1651c slide on the surface of the wheel teeth 1641a to reset. When the driving member 1650 rotates counter-clockwise, the driving end 1651a or 1651c can push the wheel teeth 1641a forward, thereby making the driving wheels 1640b and 1640a rotate synchronously and the infusion unit perform drug infusion, while driving ends 1651b and 1651d slide on the surface of the wheel teeth 1641b to reset.

Similar to the operating mode of the driving ends 1551a and 1551b described above, in the embodiment of the present invention, the front ends of driving ends 1651a and 1651c or driving ends 1651b and 1651d are not level with a distance r. Obviously, in the embodiment of the present invention, as long as there is a driving end in the driving position, this driving end can push the wheel teeth forward for drug infusion. Therefore, by adjusting the offset degree of the teeth on two driving wheels, or adjusting the distance that the driving end advances in each driving process (or that the driving end resets on the other side), the driving member 1650 has various rotation amplitudes, making the infusion unit have multiple different infusion increments.

In other embodiments of the present invention, there may be two or more driving ends disposed on the driving member 1650. When the number of driving ends is an odd number, like 3, 5, etc., the number of driving end(s) that cooperate with each driving wheel is not equal, but each driving wheel works with at least one driving end. The operating mode and working principle of the driving end on each side of the driving member 1650 can refer to the foregoing.

Figure 13A:
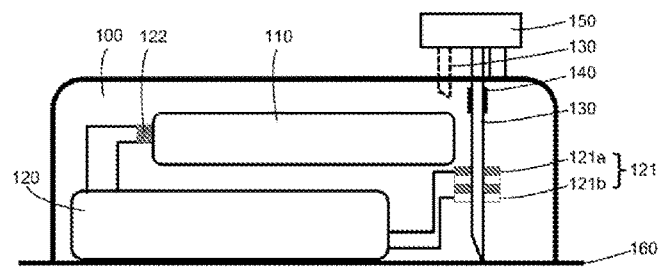
FIG. 13a is a schematic view of an infusion cannula of an integrated artificial pancreas with multiple infusion modes in a pre-installation position according to one embodiment of the present invention.
Figure 13B:
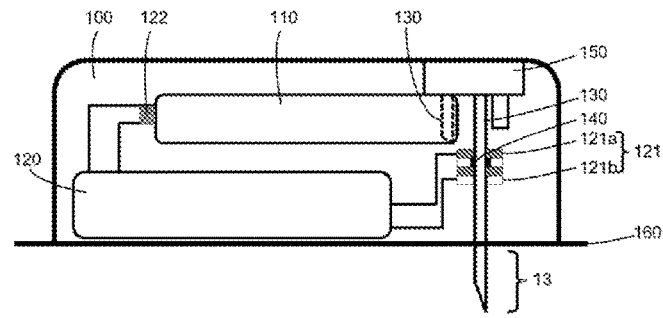
FIG. 13b is a schematic view showing the infusion cannula of the integrated artificial pancreas with multiple infusion modes in a working position according to an embodiment of the present invention.

FIG. 13a-FIG. 13b are views of an integrated artificial pancreas with multiple infusion modes 100 according to an embodiment of the present invention, and the integrated artificial pancreas with multiple infusion modes 100 is an integral structure. FIG. 13a shows the infusion cannula 130 in the pre-installation position while FIG. 13b shows the infusion cannula 130 in the working position.

Program unit 120 includes an input end 121 and an output end 122. The input end 121 is used for receiving a body fluid analyte data signal. In the embodiment of the invention, the input end 121 includes electrically connective regions 121a and 121b. When in operation, the electrically connective region is electrically connected to the electrode or electrode lead to receive the analyte signal. In other embodiments of the invention, the input end 121 may also include more electrically connective regions depending on the number of electrodes. The output end 122 is electrically coupled to the power unit allowing the program unit 120 to effectively control the drug infusion unit 110.

During the use of the integrated artificial pancreas with multiple infusion modes of the embodiment of the present invention, the infusion cannula 130 can slid relative to the input end 121, while the input end 121 is provided as an elastic member. The elastic member is to ensure an interference fit between the infusion cannula 130 and the input end 121 to avoid poor electrical contact. The elastic member includes: conductive rubber strip, oriented conductive silica gel, conductive ring, conductive ball, etc. When the number of electrodes is relatively large, the electrically connective regions are relatively dense. In this case, according to different structural designs, the elastic members may be one or more combinations of the above.

In an embodiment of the invention, the infusion cannula 130 is mounted on the mounting unit 150. When the infusion cannula 130 is in the pre-installation position, the mounting unit 150 protrudes from the outer surface of the integrated artificial pancreas with multiple infusion modes 100, as shown in FIG. 13a. When the infusion cannula 130 is installed to the working position, the mounting unit 150 is pressed into the integrated artificial pancreas with multiple infusion modes 100 with the top portion integral with the integrated artificial pancreas with multiple infusion modes 100 housing, as shown in FIG. 13b.

Prior to use by users, the mounting unit 150 holds the infusion cannula 130 in the pre-installation position. After the integrated artificial pancreas with multiple infusion modes 100 is attached on the surface of the human body, the mounting unit 150 is pressed to insert the infusion cannula under the skin, and the integrated artificial pancreas with multiple infusion modes can start operation. Compared with other infusion cannula installation methods, the installation method of the embodiment of the invention reduces the steps required for installation, makes the installation more convenient and flexible and improves the user experience.

The manner of setting the infusion cannula 130 in the mounting unit 150 can be various, and is not specifically limited herein. Specifically, in the embodiment of the present invention, the other side of the mounting unit 150 also protrudes from the partial infusion cannula 130 (shown by a dotted line in FIG. 13a and FIG. 13b) for subsequent connection with the outlet of the drug infusion unit 110 to achieve drug circulation.

In other embodiments of the invention, the infusion cannula 130 further includes an electrical contact region 140 coupled to the input end 121. As shown in FIG. 13a, the electrical contact region 140 is not electrically coupled to the input end 121 when the infusion cannula 130 is in the pre-installation position. And the other end of the infusion cannula 130 is also not connected with the drug infusion unit 110 outlet. As shown in FIG. 13b, when the infusion cannula 130 is mounted to the working position, one end of the infusion cannula 130 is inserted subcutaneously (indicated by the solid line portion of the infusion cannula in FIG. 13*b*) and the other end (illustrated by the dotted portion of the infusion cannula in FIG. 13*b*) is connected with the outlet of the drug infusion unit 110, thereby establishing a flow path for the drug from the drug infusion unit 110 to the body tissue fluid. At the same time, the electrical contact region 140 reaches the electrically connective region of the input end 121, enabling electrical connection between the program unit 120 and the electrical contact region 140.

It should be noted that even if the infusion cannula 130 and the drug infusion unit 110 are connected, and the input end 121 and the electrical contact region 140 of the infusion cannula 130 are electrically connected, as long as the infusion cannula 130 does not penetrate the skin, the program unit 120 will not enter working mode, so that the integrated artificial pancreas with multiple infusion modes does not generate any analyte data signal, nor does it issue an instruction to inject drug. Therefore, in other embodiments of the present invention, when the infusion cannula 130 is in the pre-installation position, the electrical contact region 140 may also be electrically connected to the electrically connective region of the input end 121 or the infusion cannula 130 may be coupled to the outlet of the drug infusion unit 110. And there are no specific restrictions herein.

In an embodiment of the invention, a medical tape 160 for attaching the integrated artificial pancreas with multiple infusion modes 100 to the skin surface is used to paste the program unit 120, the drug infusion unit 110, the electrode and the infusion cannula 130 as a whole on the skin. When the infusion cannula 130 is installed to the working position, the portion of the infusion cannula 130 that is inserted into the skin is 13.

Figure 14A:
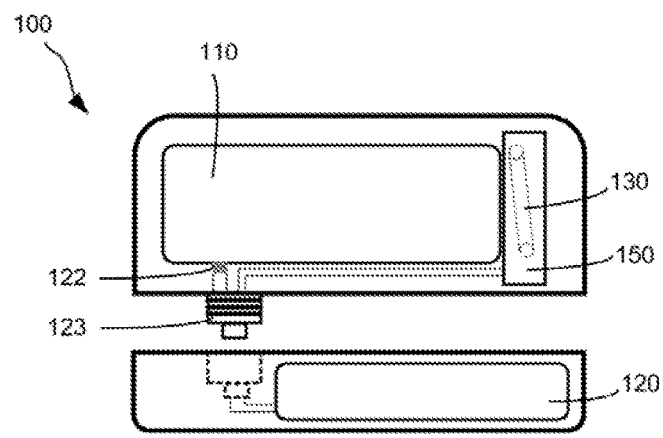
FIG. 14a-FIG. 14b are top views of an integrated artificial pancreas with multiple infusion modes in accordance with another embodiment of the present invention.

FIG. 14*a* is a top view of an integrated artificial pancreas with multiple infusion modes 100 in accordance with another embodiment of the present invention.

In one embodiment of the invention, the integrated artificial pancreas with multiple infusion modes 100 comprises two parts. The program unit 120 is disposed in one part, the drug infusion unit 110 is disposed in another part, and the two parts are electrically connected by the waterproof electrical plug 123. The part of the drug infusion unit 110 can be discarded after being used once, and the part of the program unit 120 can be reused, saving the user's cost.

In other embodiments of the present invention, the integrated artificial pancreas with multiple infusion modes 100 may also be composed of more parts, and parts that do not require electrical connection may be connected using a common waterproof plug.

Figure 14B:
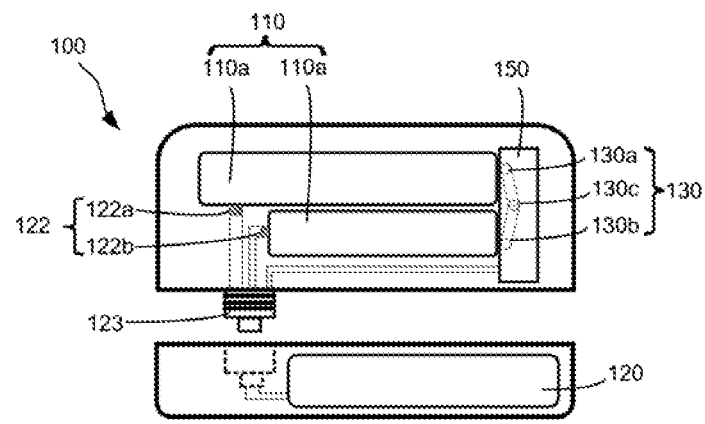

FIG. 14*b* is a top view of an integrated artificial pancreas with multiple infusion modes 100 in accordance with another embodiment of the present invention.

In an embodiment of the invention, the integrated artificial pancreas with multiple infusion modes 100 comprises two parts, and the drug infusion unit 110 comprises two infusion subunits 110*a* and 110*b*. The infusion subunits 110*a* and 110*b* can be used to reserve different drugs such as insulin, glucagon, antibiotics, nutrient solution, analgesics, morphine, anticoagulants, gene therapy drugs, cardiovascular drugs or chemotherapeutic drugs, etc. Infusion subunits 110*a* and 110*b* are electrically coupled to outputs 122*a* and 122*b*, respectively, allowing the program unit 120 to effectively control the drug infusion unit 110. The outlets of infusion subunits 110*a* and 110*b* can be connected with the 130*a* portion and 130*b* portion of infusion cannula respectively. 130*a* and 130*b* are connected with the 130*c* portion of infusion cannula, respectively. The 130*c* portion of the infusion cannula is used to penetrate the skin, thereby establishing a path for the two drugs to flow from the drug infusion unit 110 into the body fluid. That is, the infusion device still penetrates the skin only in one position. In the embodiment of the present invention, after the body fluid analyte data signal is transmitted to the program unit 120, program unit 120 can output different infusion signals to different infusion subunits to control whether infusion of drug is required. This method realizes accurate detection and control of body fluid analyte level to stabilize the physiological state of the user.

In other embodiments of the present invention, there may be more infusion subunits according to actual needs, and multiple infusion subunits may be disposed in different parts of the integrated artificial pancreas with multiple infusion modes 100. There are no specific restrictions herein.

Figure 15A:
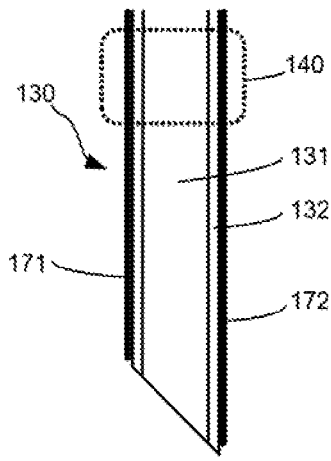
FIG. 15a-FIG. 15b are partial longitudinal views of an infusion cannula including two electrodes according to one embodiment of the present invention.
Figure 15B:
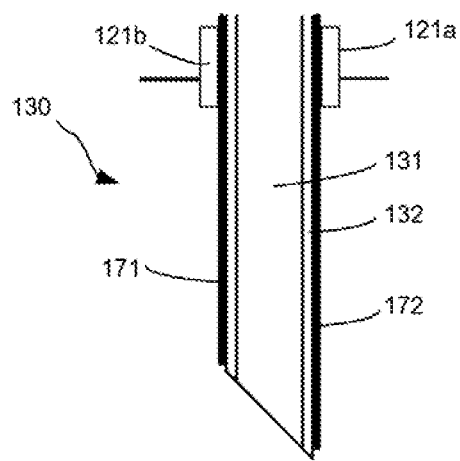

FIG. 15*a*-FIG. 15*b* are partial longitudinal views of the infusion cannula 130 including two electrodes.

In the embodiment of the invention, the integrated artificial pancreas with multiple infusion modes 100 includes at least two detecting electrodes that are disposed on the wall of the infusion cannula 130, as shown in FIG. 15*a*. The different electrodes are electrically connected to the electrically connective regions at the position of the dotted frame 140. The cavity 131 of the infusion cannula 130 is used for drug infusion.

In the embodiment of the present invention, the electrodes, such as electrode 171 and electrode 172, are plated on the outer surface of the cannula wall of the infusion cannula 130. The electrode 171 and the electrode 172, electrically insulated from each other, are directly electrically connected to the electrically connective regions 121*a* and 121*b* of the input end, respectively, which allows electrical signals of the body fluid analyte data to be transmitted to program unit 120, as shown in FIG. 15*b*. Once the puncture is performed at one position, the analyte detection and the drug infusion can be completed simultaneously, reducing the risk of the user's infection.

It should be noted that, in the embodiment of the present invention, when the infusion cannula 130 is mounted to the working position, a part of the electrode 171 or the electrode 172 is located in the subcutaneous tissue fluid, while another part is located above the skin, so that electrical signals can be transmitted on the electrode. The corresponding electrode arrangements in the other embodiments below have the same function and will not be described in detail later.

In the embodiment of the present invention, the integrated artificial pancreas with multiple infusion modes 100 has only two electrodes, the electrode 171 is a working electrode while the electrode 172 is an auxiliary electrode. In another embodiment of the invention, the electrode 171 is an auxiliary electrode while the electrode 172 is a working electrode. The auxiliary electrode is a counter electrode.

In other embodiments of the present invention, more electrodes, which are electrically insulated from each other, may be provided on the surface of the infusion cannula 130.

Figure 16A:
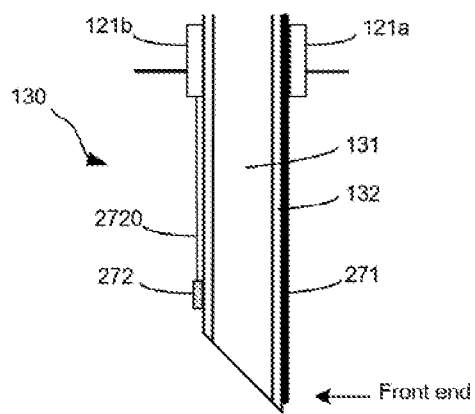
FIG. 16a-FIG. 16c are partial longitudinal views of an infusion cannula and the two electrodes in accordance with another embodiment of the present invention.
Figure 16B:
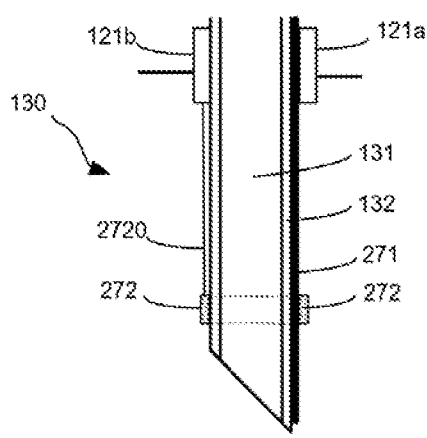
Figure 16C:
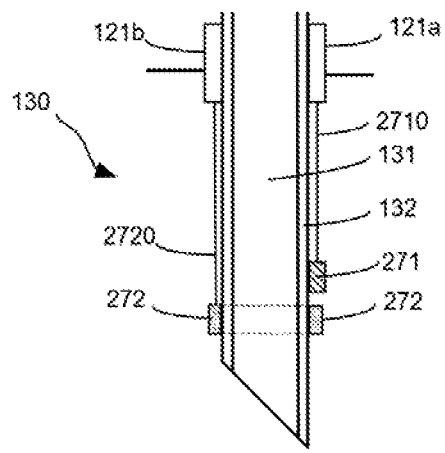

FIG. 16*a*-FIG. 16*c* are partial longitudinal views of an infusion cannula 130 in accordance with another embodiment of the present invention.

It should be noted that the electrodes or electrode leads in all embodiments of the present invention are coated or plated on the infusion cannula 130, but for ease of marking and description, the electrode leads or electrodes and the infusion cannula will be depicted separately in the FIG.s. The following related structural views are the same as those here, which will not be described in detail below.

In this embodiment, the cannula wall 132 of the infusion cannula 130 provides with the electrode 271 and the electrode 272. And the electrode 271 is directly electrically connected to the electrically connective regions 121a, such as the electrode 171 in FIG. 15a. The electrode 272 is disposed at the front end of the infusion cannula 130. And an electrode lead 2720 is used to electrically connect to the electrode 272 and the electrically connective regions 121b. When the infusion cannula 130 is mounted to the working position, the electrode 272 is located on the subcutaneous part of the outer surface of the cannula wall 132, while a part of the electrode 272 is located in the subcutaneous tissue fluid and another part is located above the skin. At this time, the electrode 272 is indirectly electrically connected to the electrically connective regions 121b, sending parameter information to the program unit.

The embodiment of the present invention does not specifically limit the shape of the electrode 272. If the electrode 272 may be ring-shaped, the electrode 272 surrounds the front end of the infusion cannula 130, as shown in FIG. 16b. At this time, an insulation layer is provided between the electrode 272 and the electrode 271. As shown in FIG. 16c, in yet another embodiment of the present invention, the electrode 271 and the electrode 272 are both provided at the front end of the infusion cannula 130, that is, on the subcutaneous part of the outer surface of the cannula wall. The outer surface of the cannula wall 132 is also provided with an electrode lead 2710 and an electrode lead 2720 that are electrically connected to the electrode 271 and the electrode 272, respectively. When the infusion cannula 130 is installed to the working position, the electrically connective regions 121a and 121b at the input end are electrically connected to the electrode lead 2710 and the electrode lead 2720, respectively. Therefore, the electrode 271 and the electrode 272 are indirectly electrically connected to the input end, transmitting the body fluid parameter signal to the program unit. During detection, both the electrode 271 and the electrode 272 are located in the subcutaneous tissue fluid.

As shown in FIG. 16c, the electrode 272 is arranged in a ring shape surrounding a part of the outer surface of the cannula wall 132. The electrode 271 and the electrode 272 may have other shapes, which is not specifically limited herein.

Figure 17:
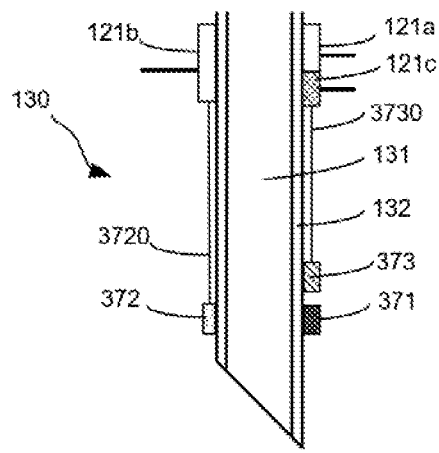
FIG. 17 is a partial longitudinal view of an infusion cannula provided with three electrodes in accordance with still another embodiment of the present invention.

FIG. 17 is a partial longitudinal view of an infusion cannula 130 provided with three electrodes in accordance with yet another embodiment of the present invention.

In the embodiment of the present invention, three electrodes are disposed on the infusion cannula 130: the electrode 371, 372 and 373 which are all disposed on the outer surface of the cannula wall 132. Similarly, the surface of the cannula wall 132 is also provided with electrode leads 3720 and 3730 which are electrically connected to the electrode 372 and the electrode 373, respectively. Similarly, the outer surface of the cannula wall 132 is also provided with an electrode lead electrically connected to the electrode 371, but it is not shown in order to simplify the marking. When the infusion cannula 130 is installed to the working position, the electrode lead of the electrode 371, electrode lead 3720 and electrode lead 3730 are electrically connected to the electrically connective regions 121a, 121b, and 121c of the input end, respectively, connecting the input end to each electrode. The shapes of the three electrodes can be various, and there is no specific limitation herein.

In the embodiment of the present invention, in order to simplify the design of the electrically connective region, the elastic member at the input end is an oriented conductive silica gel or a conductive ring. By doping different elements in the silica gel, it is possible to achieve directional conduction, such as horizontal conduction or vertical conductivity. Thus, even if 121a and 121c are adjacent to each other, the two can still be electrically insulated from each other. The electrically connective region 121b may be a conductive rubber strip or a conductive ball or the like, and is not specifically limited herein.

In the embodiment of the present invention, the electrode 371 is a working electrode, and the electrode 372 and the electrode 373 are both auxiliary electrodes. At this time, the electrode 371 and the electrode 372 or the electrode 373 may constitute a different electrode combination, that is, the two electrode combinations share the electrode 371. The program unit 120 can select different electrode combinations to detect body fluid analyte data. After the electrode combination is formed, on the one hand, when a working electrode combination fails to detect, the program unit 120 can select other electrode combinations for detection according to the situation to ensure that the detection process of the body fluid signal is uninterrupted. On the other hand, the program unit 120 can select a plurality of electrode combinations to work simultaneously, perform statistical analysis on multiple sets of data of the same parameter at the same time, improve the accuracy of the analyte data, and thereby output a more accurate drug infusion signal.

In another embodiment of the present invention, the electrode 371, electrode 372, and electrode 373 include an auxiliary electrode and two working electrodes, which can also be arbitrarily selected according to actual needs, which are not specifically limited herein.

As an embodiment of the present invention, the electrode 371 is a working electrode, the electrodes 372 and 373 are auxiliary electrodes which are used as a counter electrode and a reference electrode, respectively, thereby forming a three-electrode system. Similarly, the three electrodes can be arbitrarily selected according to actual needs, which are not specifically limited herein.

Also, in other embodiments of the invention, more electrodes may be provided. The system includes a plurality of working electrodes and a plurality of auxiliary electrodes. At this time, each electrode combination includes at least a working electrode and an auxiliary electrode, and thus a plurality of electrodes may constitute a plurality of electrode combinations. The program unit 120 may select one or more electrode combinations to detect body fluid analyte data, as desired.

Figure 18:
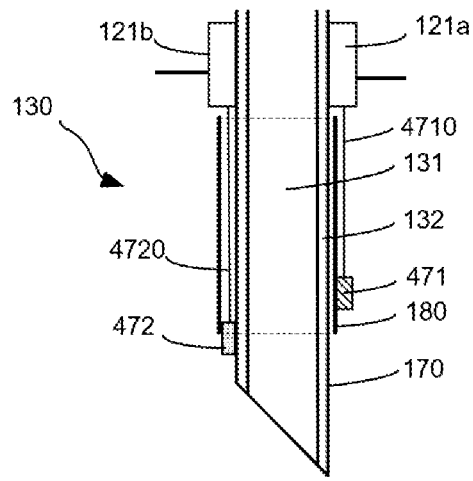
FIG. 18 is a partial longitudinal view of an infusion cannula including an inner layer cannula and one outer layer cannula in accordance with still another embodiment of the present invention.

FIG. 18 is a partial longitudinal view of an infusion cannula 130 including an inner layer cannula 170 and one outer layer cannula 180 in accordance with yet another embodiment of the present invention.

The cavity 131 of the inner layer cannula 170 is used as a drug infusion channel. The cannula wall of the infusion cannula 130 includes the inner layer cannula wall and the outer layer cannula wall. The electrode 472 is disposed outside the cannula wall of the inner layer cannula 170, while the electrode 471 is provided on the outer surface of the wall of the outer layer cannula 180. At this time, the electrode 472 is disposed in the wall of the infusion cannula 130, that is, the electrode 472 is embedded between the outer layer cannula 180 and the inner layer cannula 170.

In the embodiment of the present invention, the electrode 472 may be partially covered by the outer layer cannula 180 (as shown in FIG. 18), or completely covered by the outer layer cannula 180. The electrode 472 is electrically connected to the electrically connective region 121b through an electrode lead 4720, while the electrode 471 is electrically connected to the electrically connective region 121a through an electrode wire 4710. When the electrode 472 is partially or completely covered by the outer layer cannula 180, the wall material of the outer layer cannula 180 is a permeable membrane or a semi-permeable membrane. Such selection can facilitate the body fluid analyte to pass through the wall of the outer layer cannula 180 and to be detected by the electrode, thereby improving the flexibility of electrode position design without affecting the detection.

In another embodiment of the present invention, the electrode 471 and the electrode 472 are both disposed in the wall of the infusion cannula 130, that is, the electrode 471 and the electrode 472, which are completely covered by the outer layer cannula 180, are both embedded between the inner layer cannula 170 and the outer layer cannula 180. At this time, the material of the outer layer cannula 180 is as described above, which makes analytes detected by the electrode through the outer layer cannula 180.

It should be noted that, in other embodiments of the present invention, more layers of outer layer cannulas may be arranged outside the inner layer cannula 170. And as described above, more electrodes can be provided on the infusion cannula 130. According to actual needs, different electrodes can be arranged between different outer layer cannulas. And at least one electrode is disposed between the wall of the inner layer cannula and the outermost cannula.

In addition to embedding electrodes into the wall of the infusion cannula 130, some embodiments of the present invention can also reduce the length of the outer layer cannula 180 in FIG. 18, directly exposing the electrode 472 disposed on the outer surface of the inner layer cannula 170 in tissue fluid.

Compared with the prior arts, the technical solution of the present invention has the following advantages:

In the integrated artificial pancreas with multiple infusion modes disclosed herein, an infusion cannula provided with at least two detecting electrodes. The infusion cannula performs analyte detection and drug infusion at the same time. Once the puncture is performed at one position, the analyte detection and the drug infusion can be completed simultaneously, reducing the risk of the user's infection. Secondly, when the infusion cannula is installed to the working position, the infusion cannula connects with the drug infusion unit to allow the drugs to flow through the infusion cannula into the body, and the different electrodes are electrically connected to different electrically connective regions inputting the analyte data signal to the program unit. With this design method, after the user attaches the infusion device to the skin surface, the mounting unit for installing the infusion cannula is pressed. When the infusion cannula is installed to the working position, the infusion device can begin to work. This approach reduces the user's pre-using steps and improves the user experience. In addition, the artificial pancreas has a variety of different drug infusion rates or infusion increments, for the user or closed-loop system to choose, enhancing the user experience.

Furthermore, when the electrode located on the outer wall surface of the inner layer cannula is covered in whole or in part by the outer layer cannulas, the material of the outer layer cannulas wall is permeable membrane or a semi-permeable membrane. The cannula wall material is selected from a permeable membrane or a semi-permeable membrane to ensure the required analyte passes through the cannula wall to the electrode surface. It can improve the flexibility of electrode position design without affecting the detection.

Furthermore, a plurality of electrodes constitute one or more electrode combinations, each electrode combination includes working electrode and auxiliary electrode, and the program unit selects one or more electrode combinations to detect the body fluid analyte data. On the one hand, when a combination of electrodes fails to detect, the program unit can select other electrode combinations for detection according to the situation to ensure the detection process of the body fluid signal is uninterrupted. On the other hand, the program unit can select multiple electrode combinations to work at the same time, performing statistical analysis on multiple sets of data of the same parameter at the same time, improving the detection accuracy of the analyte data, and then issue a more accurate infusion signal.

Furthermore, the drug infusion unit comprises a plurality of infusion subunits, the plurality of infusion subunits being electrically connected to the output end respectively, and the program unit controlling whether each infusion subunit delivers drugs. Different drugs are reserved in different infusion subunits, and the program unit sends different drug infusion instructions to different infusion subunits to achieve precise control of the analyte level in body fluid.

Furthermore, the operating mode of the first driving unit includes the amplitude of the unidirectional movement, the amplitude of the reciprocating movement or the movement rate, therefore a variety of different operating modes of the first driving unit include different unidirectional movement or reciprocating movement, or various different movement rates, the user or closed-loop system can arbitrarily choose the appropriate infusion mode to accurately control the level of body fluids according to the actual requirements of the body, improving the user experience.

Furthermore, the second driving unit is movably assembled on the base, and the base and the second driving unit are frictional fit. The friction fit can increase the frictional force the second driving unit receives during its movement. When the first driving unit does not implement actually driving, the second driving unit stops moving to ensure the accuracy of the drug infusion volume and eliminate potential safety hazards.

In summary, the present invention discloses an integrated artificial pancreas with multiple infusion modes that has both infusion and detection functions to reduce the number of punctures on the skin. With only one puncture at one position, analyte detection and drug infusion can be completed, reducing the risk of infection.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. An integrated artificial pancreas with multiple infusion modes, comprising:
   a drug infusion unit, including:
   at least one drug storage unit;
   a screw connected to a piston and a driving wheel provided with wheel teeth, respectively, the driving wheel drives the screw to move by rotation, pushing the piston, provided in the drug storage unit, forward;
   a driving unit at least includes a first driving unit and a second driving unit that cooperate with each other, the second driving unit drives the screw forward, wherein the driving wheel is part of the second driving unit;

a power unit connected to the first driving unit, wherein the power unit comprises an advancing member and a reset member, wherein the advancing member is configured to apply a first force in a first direction to the first driving unit and wherein the reset member is configured to apply a second force in a second direction to the first driving unit, wherein the first force and the second force are in different directions, and the first force and the second force make the first driving unit have a variety of different operating modes, thereby making the infusion unit have various different infusion increments or infusion rates;

a program unit including input end and output end, and the input end comprises a plurality of electrically connective regions for receiving signals of analyte data in the body fluid, after the output end is electrically connected to the power unit, according to the received signals of analyte data in the body fluid, the program unit controls the pivot modes of the driving unit to implement whether the drug infusion unit delivers the drug; and an infusion cannula provided with at least two electrodes, the infusion cannula is the drug infusion channel, the electrodes are disposed on the cannula wall, when the infusion cannula is installed to a working position, the infusion cannula is connected with the drug infusion unit, the drug can then be injected into the body through the infusion cannula, and the different electrodes are electrically connected to different electrically connective regions respectively, inputting signal of analyte data in the body fluid to the program unit.

2. The integrated artificial pancreas with multiple infusion modes of claim 1, wherein
the electrodes are located on the outer surface of the cannula wall or in the cannula wall.

3. The integrated artificial pancreas with multiple infusion modes of claim 2, wherein
the electrodes are located on the outer surface of the cannula wall, and when the infusion cannula is installed to the working position, different electrodes are directly electrically connected to different electrically connective regions, respectively.

4. The integrated artificial pancreas with multiple infusion modes of claim 3, wherein
the electrodes are located on the subcutaneous part of the outer surface of the cannula wall, and the outer surface of the cannula wall is further provided with electrode leads electrically connected to the electrodes, and when the infusion cannula is installed to the working position, different electrode leads are electrically connected to different electrically connective regions, respectively.

5. The integrated artificial pancreas with multiple infusion modes of claim 2, wherein
the infusion cannula includes an inner layer cannula and at least one outer layer cannula, and the at least one outer layer cannula is disposed outside the inner layer cannula, and the inner layer cannula is used for drug infusion.

6. The integrated artificial pancreas with multiple infusion modes of claim 5, wherein
at least one electrode is provided between the outer wall of the inner layer cannula and the outermost cannula.

7. The integrated artificial pancreas with multiple infusion modes of claim 6, wherein
when the infusion cannula is installed to the working position, the electrode located on the outer wall surface of the inner layer cannula is entirely exposed in the subcutaneous tissue fluid, or covered in whole or in part by the outer layer cannulas.

8. The integrated artificial pancreas with multiple infusion modes of claim 7, wherein
when the electrode located on the outer wall surface of the inner layer cannula is covered in whole or in part by the outer layer cannulas, the material of the outer layer cannula walls is permeable membrane or a semi-permeable membrane.

9. The integrated artificial pancreas with multiple infusion modes of claim 1, wherein
the electrodes include working electrode and auxiliary electrode, and the number of the working electrode(s) and the auxiliary electrode(s) is one or more, respectively.

10. The integrated artificial pancreas with multiple infusion modes of claim 9, wherein
the auxiliary electrode is counter electrode, or the auxiliary electrode includes counter electrode and reference electrode.

11. The integrated artificial pancreas with multiple infusion modes of claim 10, wherein
a plurality of electrodes form one or more electrode combinations, each electrode combination comprising working electrode and auxiliary electrode, the program unit choosing one or more electrode combinations to detect analyte data in body fluid.

12. The integrated artificial pancreas with multiple infusion modes of claim 1, wherein
the input end is an elastic member, and the elastic member comprises one of or a combination of conductive strip, oriented conductive silica gel, conductive ring and conductive ball.

13. The integrated artificial pancreas with multiple infusion modes of claim 1, wherein
the drug infusion unit includes a plurality of infusion subunits, the plurality of infusion subunits being electrically connected to the output ends, respectively, and the program unit controlling whether each infusion subunit delivers drugs.

14. The integrated artificial pancreas with multiple infusion modes of claim 1, wherein
the integrated artificial pancreas with multiple infusion modes is composed of a plurality of parts, the drug infusion unit and the program unit are arranged in different parts, and the different parts are connected by waterproof plugs.

15. The integrated artificial pancreas with multiple infusion modes of claim 1, wherein
the operating mode of the first driving unit includes the amplitude of the unidirectional movement, the amplitude of the reciprocating movement or the movement rate, therefore a variety of different operating modes of the first driving unit include different unidirectional movement or reciprocating movement, or various different movement rates.

16. The integrated artificial pancreas with multiple infusion modes of claim 15, wherein
the first driving unit includes at least one driving end, and the second driving unit includes at least one driving wheel provided with wheel teeth, and the driving end pushes the wheel teeth forward to rotate the driving wheel.

17. The integrated artificial pancreas with multiple infusion modes of claim 16, wherein
the driving unit further includes a rotating shaft, the first driving unit includes at least two driving ends, and the second driving unit includes two fixedly connected driving wheels, and each driving wheel cooperates with at least one driving end.

18. The integrated artificial pancreas with multiple infusion modes of claim 1
further includes a base on which the second driving unit is movably assembled, and the base and the second driving unit are frictional fit.

19. The integrated artificial pancreas with multiple infusion modes of claim 18
further includes a position limited member which is movably assembled on the base to limit the position of the second driving unit, and the position limited member and the second driving unit are frictional fit.

\* \* \* \* \*